(12) United States Patent
Narasimha-Iyer et al.

(10) Patent No.: US 9,918,634 B2
(45) Date of Patent: Mar. 20, 2018

(54) SYSTEMS AND METHODS FOR IMPROVED OPHTHALMIC IMAGING

(71) Applicant: Carl Zeiss Meditec, Inc., Dublin, CA (US)

(72) Inventors: Harihar Narasimha-Iyer, Livermore, CA (US); Scott A. Meyer, Livermore, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 0 days.

(21) Appl. No.: 14/712,121

(22) Filed: May 14, 2015

(65) Prior Publication Data

US 2015/0351631 A1 Dec. 10, 2015

Related U.S. Application Data

(63) Continuation of application No. 13/453,856, filed on Apr. 23, 2012, now Pat. No. 9,055,892.

(Continued)

(51) Int. Cl.
*A61B 3/14* (2006.01)
*A61B 3/15* (2006.01)
(Continued)

(52) U.S. Cl.
CPC ............. *A61B 3/152* (2013.01); *A61B 3/102* (2013.01); *A61B 3/113* (2013.01); *A61B 3/117* (2013.01); *A61B 3/12* (2013.01)

(58) Field of Classification Search
CPC .......... A61B 3/1025; A61B 3/12; A61B 3/14; A61B 3/145; A61B 3/00; A61B 3/107;
(Continued)

(56) References Cited

U.S. PATENT DOCUMENTS 5,644,642 A 7/1997 Kirschbaum
5,943,116 A * 8/1999 Zeimer ................ A61B 3/0058
351/221

(Continued)

FOREIGN PATENT DOCUMENTS

JP 7222716 A 8/1995
JP 2003000543 A 1/2003

(Continued)

OTHER PUBLICATIONS

International Preliminary Report on Patentability received for PCT Patent Application No. PCT/EP2012/057756, dated Nov. 7, 2013, 12 pages.

(Continued)

*Primary Examiner* — Ricky Mack
*Assistant Examiner* — Robert E Tallman
(74) *Attorney, Agent, or Firm* — Morrison & Foerster LLP

(57) ABSTRACT

Systems and methods for improving ophthalmic imaging by correlating the location of a measurement on the pupil of the eye with a quality of the measurement and further controlling subsequent measurements based on the quality are presented. Aspects of the invention include obtaining optical coherence tomography (OCT) measurements through cataracts or other media opacities, obtaining B-scans with minimized tilt, and automated OCT data acquisition of select structures in the eye. Embodiments of the invention directed towards imaging tissues with angle dependent layer contrast and mapping the size and location of cataracts in the eye are also described.

18 Claims, 8 Drawing Sheets

Related U.S. Application Data

(60) Provisional application No. 61/479,788, filed on Apr. 27, 2011, provisional application No. 61/536,776, filed on Sep. 20, 2011.

(51) Int. Cl.
  *A61B 3/113* (2006.01)
  *A61B 3/10* (2006.01)
  *A61B 3/117* (2006.01)
  *A61B 3/12* (2006.01)

(58) Field of Classification Search
  CPC ......... A61B 3/11; A61B 3/111; A61B 3/1225; A61B 3/1015
  USPC ....................................................... 351/206
  See application file for complete search history.

(56) References Cited

U.S. PATENT DOCUMENTS

| | | | |
|---|---|---|---|
| 7,365,856 B2* | 4/2008 | Everett | A61B 3/102 250/227.19 |
| 7,480,396 B2 | 1/2009 | Teiwes et al. | |
| 7,805,009 B2 | 9/2010 | Everett et al. | |
| 9,033,510 B2 | 5/2015 | Narasimha-iyer et al. | |
| 2004/0012853 A1 | 1/2004 | Garcia et al. | |
| 2005/0024586 A1* | 2/2005 | Teiwes | A61B 3/113 351/209 |
| 2007/0291277 A1 | 12/2007 | Everett et al. | |
| 2008/0284981 A1* | 11/2008 | Fercher | A61B 3/102 351/221 |
| 2009/0285354 A1 | 11/2009 | Hirose et al. | |
| 2010/0110381 A1 | 5/2010 | Motamedi et al. | |
| 2010/0290007 A1 | 11/2010 | Van de Velde | |
| 2011/0001930 A1 | 1/2011 | Levecq | |
| 2011/0102742 A1 | 5/2011 | Miyasa et al. | |
| 2011/0176107 A1* | 7/2011 | Yoshida | G01N 21/4795 351/206 |
| 2011/0299034 A1 | 12/2011 | Walsh et al. | |

FOREIGN PATENT DOCUMENTS

| | | |
|---|---|---|
| JP | 2006055547 A | 3/2006 |
| JP | 2007516049 A | 6/2007 |
| JP | 2007313208 A | 12/2007 |
| JP | 2010151713 A | 7/2010 |
| JP | 2011515194 A | 5/2011 |
| WO | 1998/022016 A2 | 5/1998 |
| WO | 2009/120543 A1 | 10/2009 |

OTHER PUBLICATIONS

Advisory Action received for U.S. Appl. No. 13/453,856, dated Dec. 26, 2014, 3 pages.
Final Office Action received for U.S. Appl. No. 13/453,856, dated Oct. 9, 2014, 12 pages.
Non-Final Office Action received for U.S. Appl. No. 13/453,856, dated Apr. 28, 2014, 20 pages.
Notice of Allowance received for U.S. Appl. No. 13/453,856, dated Feb. 17, 2015, 11 pages.
Choma et al., "Sensitivity Advantage of Swept Source and Fourier Domain Optical Coherence Tomography", Optics Express, vol. 11, No. 18, Sep. 8, 2003, pp. 2183-2189.
Leitgeb et al., "Ultrahigh Resolution Fourier Domain Optical Coherence Tomography", Optics Express, vol. 12, No. 10, May 17, 2004, pp. 2156-2165.
Li et al., "Starburst: A Hybrid Algorithm for Video-Based Eye Tracking Combining Feature-Based and Model-Based Approaches", Vision for Human-Computer Interaction Workshop (in conjunction with CVPR), 2005, pp. 1-8.
Liao et al., "Robust Pupil Detection for Gaze-based User Interface", EGIHMI '10 Proceedings of the 2010 Workshop on Eye Gaze in Intelligent Human Machine Interaction, 2010, 6 pages.
Lujan et al., "Henle's Fiber Layer Revealed Using Spectral Domain Optical Coherence Tomography", ARVO Abstract #1201, 2010, pp. 1-2.
Lujan et al., "Revealing Henle's Fiber Layer Using Spectral Domain Optical Coherence Tomography", Investigative Ophthalmology & Visual Science, vol. 52, No. 3, Mar. 2011, pp. 1486-1492.
International Search Report and Written Opinion received for PCT Patent Application No. PCT/EP2012/057756, dated Nov. 27, 2012, 16 pages.
Invitation to Pay Additional Fees received for PCT Patent Application No. PCT/EP2012/057756, mailed on Sep. 24, 2012, 6 pages.
Zhu et al., "Robust Pupil Detection using a Curvature Algorithm", Computer Methods and Programs in Biomedicine, vol. 59, 1999, pp. 145-157.
Office Action received for Japanese Patent Application No. 2014-506885, dated Mar. 15, 2016, 5 pages (2 pages of English Translation and 3 pages of Official Copy).

\* cited by examiner

SYSTEMS AND METHODS FOR IMPROVED OPHTHALMIC IMAGING

PRIORITY

This application is a continuation of U.S. patent application Ser. No. 13/453,856, filed Apr. 23, 2012, which claims priority to U.S. Provisional Application Ser. No. 61/479,788, filed Apr. 27, 2011, and U.S. Provisional Application Ser. No. 61/536,776, filed Sep. 20, 2011, all of which are hereby incorporated by reference.

TECHNICAL FIELD

One or more embodiments of the present invention relate generally to improvements in the quality of data acquisition in ophthalmic diagnostic systems. In particular, it is an object of the present invention to automate the process of finding the best position to take optical coherence tomography measurements as well as maintaining that position over the acquisition time to ensure that the optimal signal for a particular type of measurement is obtained and maintained, allowing measurements to be taken automatically, without user intervention, and in the presence of media opacities. Embodiments related to imaging tissues with angle dependent reflectivity are also considered.

BACKGROUND

In optical coherence tomography (OCT) imaging, effort is placed on obtaining high image quality to allow for reproducible and clear visualization of structures and pathologies as well as quantitative measurements of features and layers within the eye. Typically OCT measurements of the posterior section of the eye are made with the focus of the beam in the plane of the pupil and the beam entering through the center of the pupil. In theory this allows the largest possible entry and exit pupil, allowing for optimal collection of the OCT signal as well as any additional signals used for alignment purposes. The resulting retinal image shows bands of varying reflectivity signals that have been correlated to layers identified in histology. Segmentation of the retinal tissue is typically made based on the observed reflectivity differences between layers, although information about the expected configuration of the layers may also be used. It has recently been recognized that the reflectivity of some structures in the eye may depend on the local tilt of the retina relative to the OCT beam.

Although a central entry point is nominally optimal, there are a number of reasons to use entry points that are not central. In subjects with media opacities such as cataracts, the measurement beam may not pass well through the opacity. In such cases, it is sometimes possible to steer the measurement beam through a different entry position so that the opacity is avoided. In other subjects, the shape of the eye may be such that the image of the retinal tissue appears tilted. A different entry point in the pupil may result in a flatter image. Because layer measurements are typically made along A-scans, a flatter retina may result in measurements with less geometrical error. Furthermore, since many OCT systems have decreasing signal quality further from the zero delay, a flatter retina may have better uniformity of intensity across the B-scan. Finally, some tissues in the eye have reflectivity that depends on the angle of incidence. Ensuring a flat retina on each visit reduces the variance of incidence angle over multiple visits, which reduces the impact of directional reflectivity on the variability of measurements made on the image. Alternately, optimal imaging of tissues with strong directional reflectivity may require a specific angle of incidence which by geometry requires a different pupil entry location, or may even require scans with multiple angles of incidence (and therefore multiple pupil entry locations) to be combined prior to layer detection.

In current systems, the user has to manually adjust the pupil entry position and find the "best" entry position for the particular subject and imaging application by a trial and error method. This is a subjective procedure, in which the operator has to review the OCT scan, the fundus image, and the iris image in order to determine the alignment that results in an optimal compromise between OCT signal quality, B-scan tilt, and fundus image quality. Though it is not current practice, in the future users may also wish to optimize based on the specific reflectivity profile of given layers.

Once the best position is identified, it is still difficult to maintain the entry position for the duration of the scan because of eye motions or changes in gaze. This effect is particularly important in OCT systems where the scans usually take a few seconds and a dense cube of data is acquired.

Various attempts have been made to increase feedback to the operator and automate aspects of data acquisition to achieve the highest quality images possible. Retinal tracking systems have been described (see for example US Patent Publication No. 2005/0024586, U.S. Pat. No. 7,480,396 and U.S. Pat. No. 7,805,009, and U.S. patent application Ser. No. 13/433,127, filed Mar. 28, 2012, hereby incorporated by reference) to compensate for motion of the retina during retinal imaging. However, retinal tracking methods usually work by analyzing images of the back of the eye that are mostly obtained by point scanning or line scanning devices that also depend on an optical path that goes through the pupil. If the scan entry position is not optimal, the images used for tracking the retina will also be affected, resulting in poor quality of tracking or a total failure to track if the fundus image quality degrades significantly.

It is therefore an object of the current invention to address some of the limitations described above. In particular, it is an object of the present invention to automate the process of finding the best position to take OCT measurements as well as maintaining that position over the acquisition time to ensure that the optimal signal is obtained and maintained, allowing measurements to be taken automatically and without user intervention. This invention further makes it possible to have a set of scan patterns optimized for different structures in the eye and allows the system to automatically place the beam at the optimal angle for each scan pattern. The information from the scans taken at multiple locations through the pupil can also be combined to produce a comprehensive view of the eye. The invention further makes it possible to ensure that a scan acquired on a future visit is acquired with the same pupil entry position, reducing any effect that variability of pupil entry location has on the variability of image quality or on variability of quantitative measurements.

SUMMARY

The invention described herein relates to a system and method to improve the visualization of different structures in the eye using a new acquisition strategy. The invention addresses the problems described above and includes methods that could fully automate the data acquisition process even for subjects with media opacities while also helping to improve the quality of the ophthalmic images. A further aspect of this invention is to propose methods to optimize the data acquisition for specific structures in the eye depending on the anatomy. Embodiments of the invention directed towards imaging tissues with angle dependent layer contrast and mapping the size and location of cataracts in the eye are described.

One aspect of the invention is correlating the pupil location associated with a particular OCT measurement with the quality of that measurement. This correlation has many potential applications including three that will be described in detail below: imaging through cataracts and other media opacities, creating automated scan algorithms to image particular locations in the eye, and obtaining low tilt B-scans. It will be readily appreciated by someone skilled in the art that the basic components of the invention would have other possible embodiments that would fall within the scope of the invention.

The main components of the pupil tracking system described herein are illustrated in FIG. 1 and are briefly discussed here. The system includes an imaging system 101 to obtain an image of a portion of the eye 103, a processing unit to identify a feature in the image (pupil detection unit 104), a system to follow the eye location in (x,y,z) over time (pupil location tracking 105), a measurement unit 102, and a measurement quality determining unit to determine the optimized measurement location 106. It is assumed that the measurement system and imaging system are calibrated so that the relationship between them is known. In the preferred embodiment, the anterior portion of the eye is imaged, the feature is the pupil, and the location of the eye is tracked using a series of the images. The measurement system of the preferred embodiment is optical coherence tomography (OCT). It is to be appreciated that other systems or combinations of systems could fall within the scope of the invention. The systems and methods described herein could be implemented automatically or via input from an instrument operator.

A first aspect of the invention is to obtain optimal signals from an ophthalmic measuring device in the presence of cataracts and other media opacities. As the first step, an image including the pupil of the eye is collected. Next the boundaries of the pupil are segmented. Using the segmentation of the pupil, it is possible to direct the measurement beam to pass through different points on the pupil. The resulting signals can be analyzed to find the best position on the pupil to make measurements. This can be achieved by looking at the characteristics of the returned measurement signal (such as strength or quality of the returned A-Scans for OCT). Once the best position is determined, the pupil location tracking will maintain the measurement beam location of the particular position on the pupil to continue acquiring the optimal measurement signal even in the presence of movement or changes in gaze. This can be accomplished with any type of pupil segmentation and gaze tracking. While this embodiment is directed towards selecting a specific pupil entry position based on a quality of the measurement data, the methods can be generalized to maintain any measurement beam location including the center of the pupil, a user selected pupil location, or a pupil location that is the same as that of a prior scan.

A further aspect of the present invention is to use the tilt of the B-scan as a quality metric for a series of measurements on different locations on the pupil. In so doing, a pupil location with minimal tilt can be selected and tracked during an OCT measurement.

Another aspect of the present invention is the ability to control the angle of the measurement beam based on a particular structure of which a measurement is desired. By changing the location of the measurement beam on the pupil, it is possible to make the measurement beam go at various angles to the optical axis thereby making the measurement beam perpendicular to different structures in the eye. This results in better visualization of different structures that are sensitive to the orientation of the measurement beam relative to the surface. The pupil location tracking unit allows tracking the motion of the patient and hence obtaining the scans at different angles reliably. Further because of the pupil location tracking, it will be possible for the system to keep track of the different angles with which the images were obtained and potentially build a composite image that includes information from the different scans.

DETAILED DESCRIPTION

The invention described herein is directed towards improving ophthalmic imaging by correlating the location of a measurement on the pupil of the eye with a quality of the measurement and further controlling subsequent measurements based on the quality. This has several important applications in the field of ophthalmic imaging including imaging through cataracts or other media opacities, obtaining B-scans with minimized tilt, and automated data acquisition of select structures in the eye. The invention could result in significantly better data acquisition as well as improved ease of use for the operator. Each application will be described in detail below.

While the invention described herein is applicable to any ophthalmic diagnostic device that needs to send a measurement signal into the eye and record the results, the preferred embodiments described herein will be focused on the field of Optical Coherence Tomography (OCT). OCT is a non-invasive, in-vivo imaging technique that is based on the back-scatter or reflectivity of light in a medium. OCT is particularly valuable in ophthalmic examinations, where the beam of light produced by the OCT device scans the eye through the pupil and the image formation process records the back-scattering profile of the light at each location. The intensity of the back-scattered light is indicative of the scattering properties of the tissue and tissue boundaries, and a grayscale cross-sectional image is formed as the light beam sweeps across the field of view (FOV). OCT imaging has dramatically advanced ophthalmic diagnostic capabilities and led also to better understanding of ocular anatomy. It is an established basis of routine ophthalmic practice.

Figure 1:
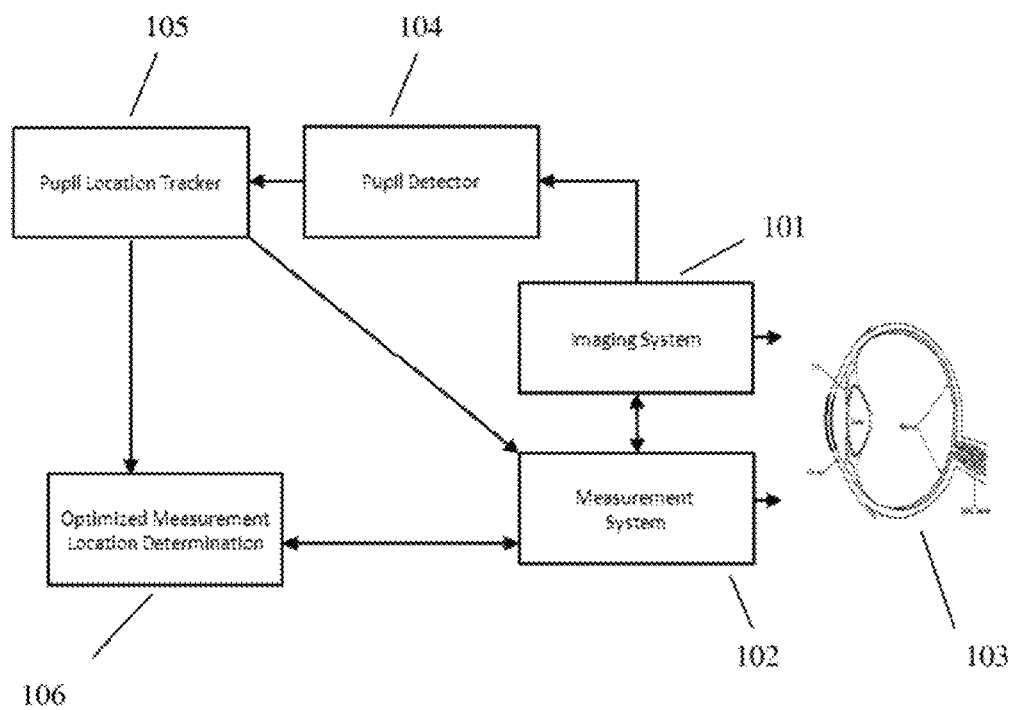
FIG. 1 shows a block diagram of a pupil tracking system of the present invention.

FIG. 1 illustrates a block diagram summarizing the present invention. Each component will be described in detail below.

Imaging System

Figure 2:
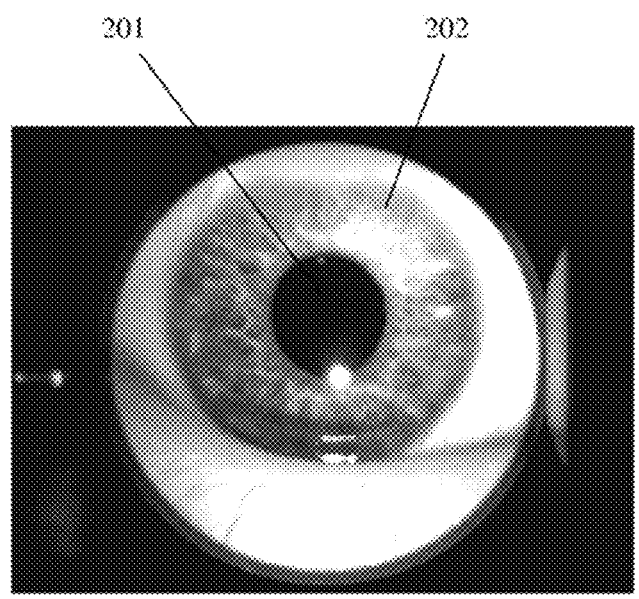
FIG. 2 is an image of the anterior of the eye that can be used in the present invention.

In the preferred embodiment of the present invention, the imaging system 101 is responsible for obtaining an image of the anterior portion of the eye 103. Structures of the anterior part of the eye such as cornea, pupil and iris will be visible in this image. The field of view of this image can be variable depending on the application but should have sufficient field of view to image the structures mentioned above at a minimum. FIG. 2 shows a sample image of the front part of the eye that is applicable to the present invention. The image shows the pupil 201, and iris 202. The cornea is the overlying transparent structure. These types of images obtained by the imaging system of the front part of the eye will be referred to as "iris-images" in the rest of the description for simplicity.

In another embodiment of the invention, the imaging system could also have visible light or infra-red illuminators that can create reflexes from the anterior part of the eye that are visible in the image. The location of the reflexes could be segmented and used for determining the gaze of the eye. In other embodiments of the invention, the imaging system could also be used to obtain images of the back portion of the eye. These images could be used for instance to track the retina and compensate for motion.

Measurement System

The measurement system 102 is responsible for obtaining the measurement of interest. A "measurement" need not be a quantitative value and could be simply an image but the term measurement is used to distinguish from the imaging system previously described. Measurements can be made in various locations in a subject's eye including the anterior and posterior sections. The invention could equally be applied to a variety of measurement systems by one skilled in the art. The measurement system will be spatially aligned with the imaging system; i.e. the relationship between the image coordinates of the imaging system and the measurement system will be well established through calibration procedures. The measurement system can also be synchronized in time to the imaging system. For the preferred embodiments described here, the measurement system is an OCT system. A basic arrangement of the OCT system is discussed below with reference to FIG. 3. The OCT system may be configured to obtain images of the posterior pole, with the OCT beam entering through the pupil. The OCT system may be configured to obtain images of the anterior segment, with the OCT beam placed relative to the pupil location. The anterior segment configuration may be enabled by addition of an external lens, an internal lens, or the removal of a lens from the posterior imaging configuration.

Figure 3:
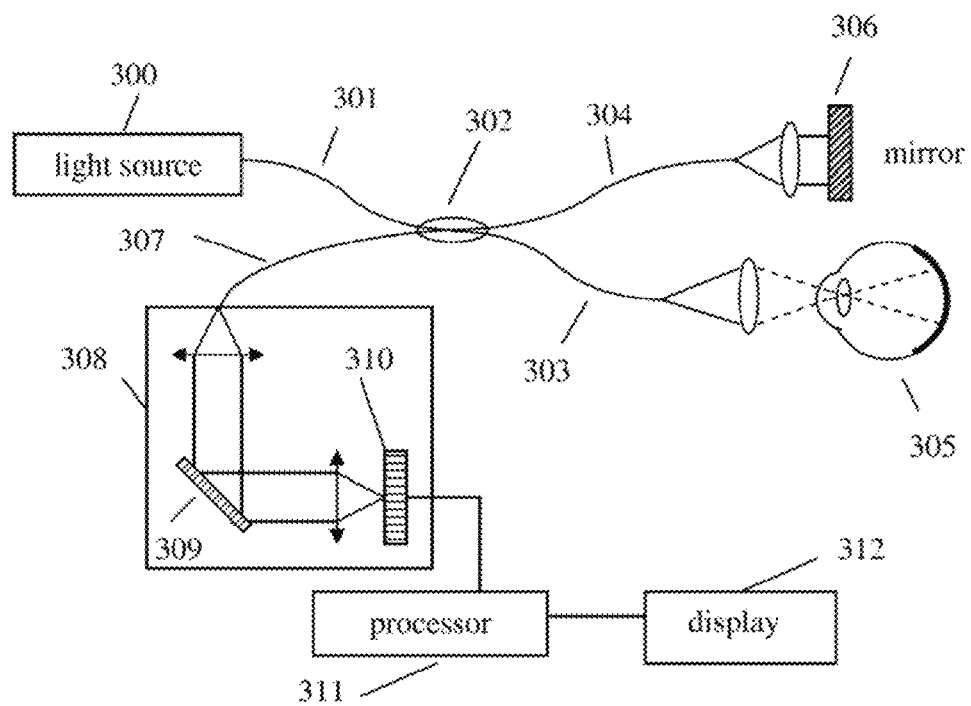
FIG. 3 shows the basic components of an SD-OCT system that could be used to acquire measurement data in various embodiments of the present invention.

Several implementations of OCT have been developed including time domain (TD-OCT) and frequency domain (spectral domain (SD-OCT) and swept-source (SS-OCT)). FIG. 3 shows a basic block diagram for a spectrometer based SD-OCT system. The light source 300 provides broad bandwidth light to a short length of an optical fiber 301 to an input port of a fiber optic coupler 302, which splits the incoming light beam into the two arms of an interferometer. The two arms each have a section of optical fiber 303 and 304 that guides the split light beam from the fiber coupler 302 to the eye of a patient 305 and a reference reflector 306 respectively. For both the sample arm and the reference arm, at the terminating portion of each fiber, there may be a module containing optical elements to collimate or focus or scan the beam. The returned light waves from the sample 305 and the reference reflector 306 are directed back through the same optical path of the sample and reference arms and are combined in fiber coupler 302. A portion of the combined light beam is directed through a section of optical fiber 307 from the fiber coupler 302 to a spectrometer 308. Inside the spectrometer, the light beam is dispersed by a grating 309 and focused onto a detector array 310. The collected data is sent to a processor 311 and the resulting processed data can be displayed on a display 312 or stored in memory for future reference and processing. Although the system of FIG. 3 includes a reflective reference arm, those skilled in the art will understand that a transmissive reference arm could be used in its place.

The interference between the returned light waves from the sample and reference arms causes the intensity of the combined light to vary across the spectrum. The Fourier transform of the interference spectrum reveals the profile of scattering intensities at different path lengths, and therefore scattering as a function of depth in the sample (see for example Leitgeb et al., "Ultrahigh resolution Fourier domain optical coherence tomography," *Optics Express* 12(10):2156 2004). The profile of scattering as a function of depth is called an axial scan (A-scan or A-line). A set of A-scans measured at neighboring locations in the sample produces a cross-sectional image (tomogram or B-scan) of the sample. Note that the principle of operation of a tunable laser based swept source OCT is very similar to that of a spectrometer based spectral domain OCT system (see for example, Choma et al. "Sensitivity advantage of swept source and Fourier domain optical coherence tomography." *Optics Express* 11(18): 2183-2189 2003), hence the spectral domain OCT system for obtaining the 3D image data set can also be a swept source OCT system or any type of OCT system.

Pupil Detection Module

The pupil detection system 104 detects the position of the pupil in the iris images collected from the imaging system. Many methods have been proposed to segment the pupil from images of the eye (see for example Wen-Hung L. et al. "Robust Pupil Detection for Gaze-Based User Interface" International IUI 2010 Workshop on Eye Gaze in Intelligent Human Machine Interaction or Zhu et al. "Robust Pupil Detection using a Curvature Algorithm" *Computer Methods and Programs in Biomedicine* 59: 145-157 1999 or Li et al. "Starburst: A hybrid algorithm for video-based eye tracking combining feature-based and model-based approaches" *Vision for Human-Computer Interaction Workshop* 2005). In one embodiment of this invention, the eye is illuminated with visible light and so the pupil appears dark against the comparatively lighter iris region in the collected image. The dark pupil can be segmented by first finding a dark blob in the image using intensity based segmentation such as clustering and connected components. After this step, the algorithm could optimize for the edges of the detected blob and finally fit a model to the boundary points. The model could be a simple circle or an ellipse.

Figure 4:
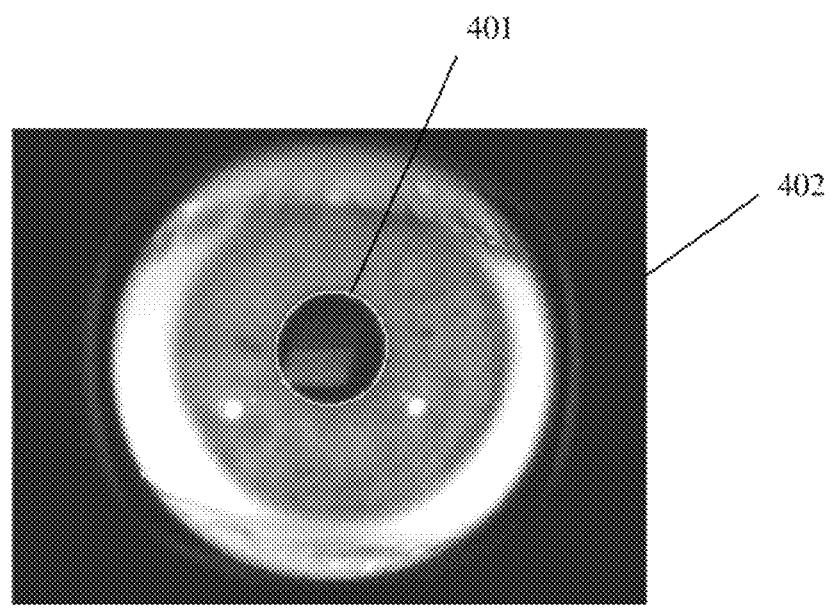
FIG. 4 shows a segmentation of the pupil in an image of an eye.

It is possible to adopt robust methods to fit the selected model to the boundary points and hence make the segmentation very accurate. It is not an objective of this invention to propose a new pupil segmentation method but rather to propose a novel way of using the segmentation information. Those skilled in the art can envision using any of a number of described algorithms in the literature for obtaining the segmentation of the pupil. The segmentation essentially provides us with coordinates of the center of the pupil as well as information on the edges of the pupil at any given point. FIG. 4 shows an example of a segmentation where the segmentation of the pupil 401 is overlaid on the original iris image 402.

Pupil Location Tracking Module

The pupil location tracking module 105 tracks the location of the pupil ideally in the lateral (x and y) and axial (z) directions. In one embodiment, this is accomplished by tracking the translational pupil position in x and y by comparing the pupil location in multiple iris images collected from the imaging system. This information can then be passed back to the measurement system to re-position the instrument or patient to compensate for the variation in location. Another embodiment would be a gaze tracking system that combines the pupil segmentation and segmentation of one or more corneal reflexes produced from suitably placed visible or infra-red illuminators on the eye of the patient. These illuminators could be part of the imaging system and could be synchronous or asynchronous with the image acquisition. A further embodiment of the invention would be to combine the pupil tracking module with a retinal tracking module that can determine the fixation very accurately. This provides a more accurate determination of the patient's gaze. These combined tracking results can be passed to the measurement module to further improve data acquisition.

Optimized Measurement Location Determination

Typically OCT measurements are made by directing the measurement beam through the center of the pupil as described in US Patent Publication No. 2007/0291277 hereby incorporated by reference. In this case an iris viewer was used to aid in the manual positioning of the OCT treatment beam. A cataract could be located in the center of the pupil reducing the quality of an OCT measurement taken at that point. A key aspect of the invention described herein is to use the fact that different pupil entry positions give different measurement signals and hence it will be possible to find an optimal pupil entry position by sampling different entry positions. Since the pupil segmentation is available, this can be done automatically and efficiently via an optimized measurement location determination module 106.

Figure 5:
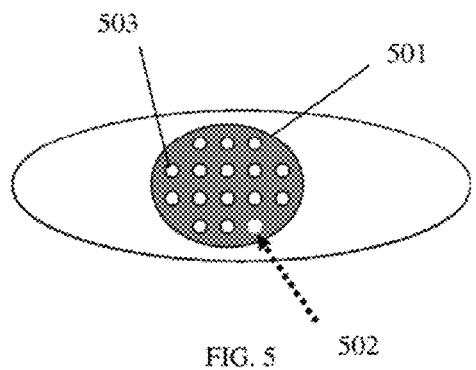
FIG. 5 shows one scanning pattern applicable to the present invention.

Consider the sampling pattern of entry positions shown in FIG. 5. The figure shows a uniform grid of pupil entry locations 503 of lateral (x and y) extend across the pupil of the eye 501. Let us denote each of these pupil entry locations as $PE_i$, where i corresponds to the index of the location. For each of the pupil entry locations, we can also record the measurement signal. The corresponding measurement signal is denoted as $M_i$.

The optimal pupil entry location can now be determined by defining an optimality condition on the measurement signal.

$$PE^* = \text{Max}_i\{Q(M_i)\},$$

Where Q(.) is a quality function that can be defined for any type of measurement signal. In words, the best pupil entry location is the one that gives the best measurement signal. In the example shown in FIG. 5 the best position is indicated with an arrow 502. The definition of "best" being defined by the choice of the quality function Q(.). The framework is general and hence can be used for any type of measurement signal. For example, if the measurement system is an FD-OCT system, each measurement signal will be an A-line.

For an OCT system with an A-line as the measurement signal, the quality function may be defined as the Signal to Noise Ratio (SNR).

$$Q(M_i) = SNR(M_i)$$

The SNR may be calculated based on a very rough segmentation of the signal from the A-line into signal and noise components. The SNR can be defined as:

$$SNR(M_i) = \frac{\text{Mean}(M_i^{signal})}{\sigma(M_i^{noise})},$$

Where Mean( ) function is the averaging function, $M_i^{signal}$ is the useful data in the measurement signal and $M_i^{noise}$ is the noise part of the measurement signal. $\sigma(M_i^{noise})$ is the standard deviation of the noise.

Figure 6:
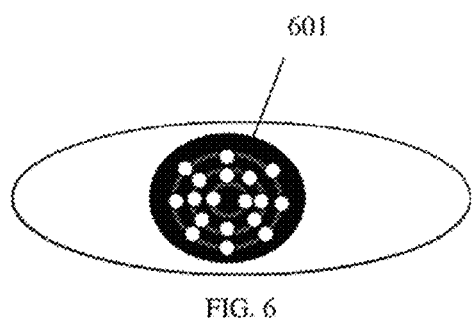
FIG. 6 shows an alternative scanning pattern applicable to the present invention.

This is only one implementation of the invention and those skilled in the art can define quality functions suited to the application and the type of measurement signal under consideration. Additionally, it is not necessary that the sampling pattern used is a uniform grid. Another possibility is shown in FIG. 6, with a series of measurements taken along concentric ring scanning patterns 601. It should be noted that FIGS. 5 and 6 display only representative scan patterns and the invention is applicable to any sampling pattern.

Once the optimal pupil entry position is determined, the measurement system can acquire data with the desired pupil entry position. The pupil location tracking system 104 can then be engaged to track the position of the pupil and hence maintain the pupil entry location at the optimal location. This position can be maintained for a single measurement session, throughout a single visit, or can be recalled for precise positioning of the measurement beam on repeat or follow-up visits.

Figure 7:
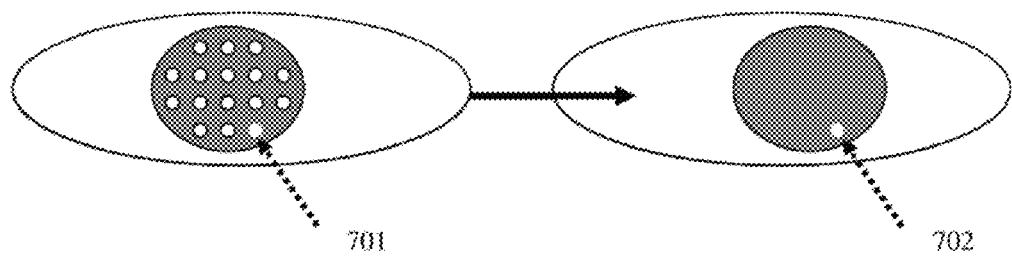
FIG. 7 illustrates how the present invention can be used to maintain the location of an ophthalmic diagnostic system in the presence of movement of the pupil of the eye.

FIG. 7 illustrates how the entry point of the measuring beam on the pupil is maintained over time. The image on the left shows the initial position of the eye and the determined "best" pupil entry position indicated with an arrow 701. The image on the right shows how the patient's gaze has wandered, and hence the pupil has moved over time (pupil shifted to right relative to the center of the eye). However, the pupil location tracking ensures that a lock is obtained on the optimal pupil entry position 702 to acquire the data.

While the methods described in this section are focused on selecting a specific measurement beam location based on a quality of the measurement data, the basic concepts can be generalized to maintain any measurement beam location over time or multiple visits. This could be the center of the pupil or a location on the pupil selected by the user. Furthermore, the system could check to insure that the user selected point lies within the boundaries of the pupil in order to reduce vignetting that will occur if the beam width is partially or entirely blocked by the iris.

Figure 8:
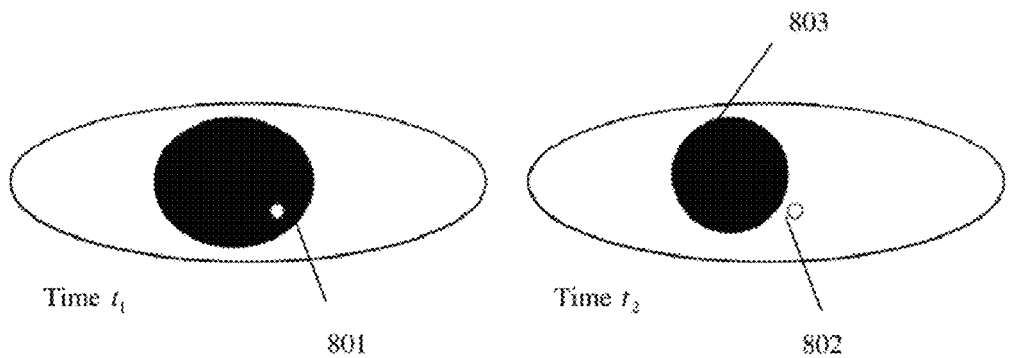
FIG. 8 illustrates how pupil constriction can lead to problems in collecting images in the same location over time.

One possible issue when trying to image through the same location of the pupil is that the pupil is inherently changing in size due to the accommodation of the iris where by it adjusts to different lighting and external conditions. In such cases the tracked location might need to be adjusted to ensure that a measurement is still possible. For example consider the case shown in FIG. 8, where the pupil constricts between two times, $t_1$ (left) and $t_2$ (right). In this case if the original pupil location 801 is maintained, this will result in no measurement signal being recorded since the location 802 exists outside the boundaries of the constricted pupil 803. In cases like this, there are three options—the first one is to wait till the pupil dilates so that the same entry position can be maintained.

Figure 9:
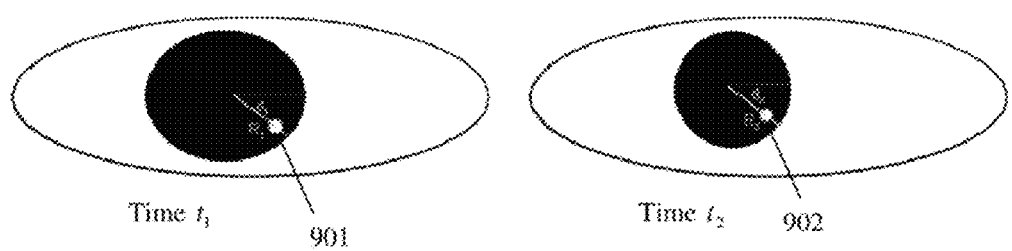
FIG. 9 shows one approach to dealing with the problem of pupil constriction while attempting to maintain the same pupil entry location in subsequent measurements of the eye.

In a second option to handle pupil constriction, the optimal pupil entry location can be scaled with respect to the pupil center as illustrated in FIG. 9. Suppose the optimal pupil entry location 901 at time $t_1$ (left image) is at a distance $d_1$ from the center of the pupil and at an angle $\theta$ to the horizontal. Let the radius of the pupil at that particular angle be $R_1$. Now let us consider that the pupil has constricted at time $t_2$ (right image) and the new radius along the same angle is $R_2$. Assuming the pupil is constricting uniformly around the center, the new optimal position 902 can be found as:

$$d_2 = \frac{d_1}{R_1} R_2.$$

Here it is assumed that the angle $\theta$ remains the same for the new optimal entry position.

Figure 10:
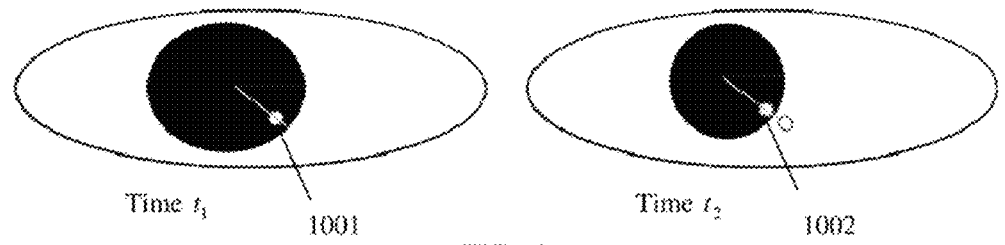
FIG. 10 shows an alternative approach to dealing with the problem of pupil constriction while attempting to maintain the same pupil entry location in subsequent measurements of the eye.

The third option to handle this problem is illustrated in FIG. 10 for initial pupil entry position 1001 at time $t_1$. At time $t_2$, it is possible to search along the line defined by angle $\theta$ from the horizontal and find the point 1002 nearest to the old position and that lies inside the new boundary of the pupil.

Reduced Tilt Measurements

The entry point of the pupil is related to the incident angle of the OCT beam on the retina, and as a result, the entry point is related to the apparent tilt of the retina in the acquired image. Although for many subjects, the flattest acquired image is obtained by entering the pupil through the center, the anatomy of some eyes is such that a flat OCT B-scan may not be obtained at the center of the pupil, but at some off-center position. A quality metric can be established to obtain the OCT B-Scans as flat (least tilt) as possible. Since the OCT signal sensitivity differs based on the location of the tissue in z, it is highly desirable to have all the tissue that is being imaged at the same depth or as flat as possible. As will be described in detail below, another property of OCT is the change in signal caused due to directional reflectivity of the different structures being imaged. A flat scan would ensure that the direction of incidence of the OCT beam is approximately uniform throughout the scan and thus enables a better comparison between the reflectance from the different structures.

Figure 11:
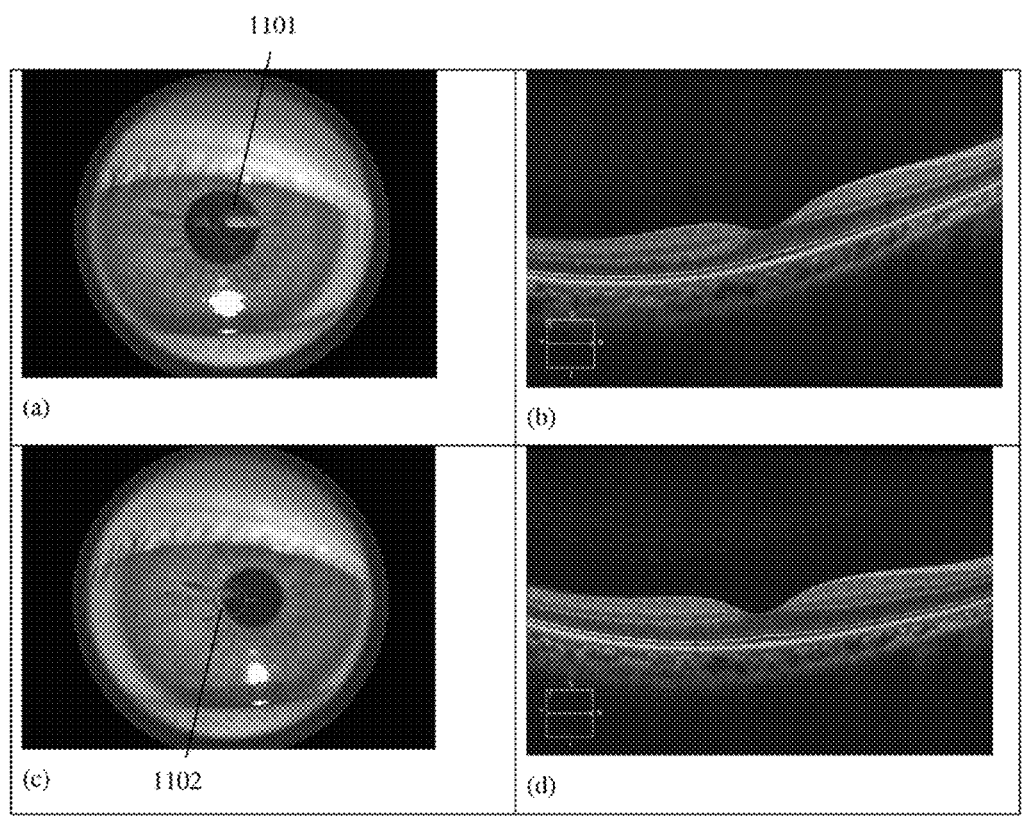
FIG. 11 illustrates how the pupil entry position can affect the tilt of the retina in the resulting B-scans acquired at each location.

It has been seen that the tilt of the B-Scan can be changed by varying the pupil entry position. (see for example Lujan, et al. "Revealing Henle's Fiber Layer using Spectral Domain Optical Coherence Tomography" *Investigative Ophthalmology & Visual Science* 52(3) March 2011 1486-1492). FIG. 11 shows B-Scans through the same location of the retina but at different pupil entry positions illustrating the tilt effect. FIG. 11(*a*) shows the location on the pupil where the OCT image in FIG. 5(*b*) was acquired. The resulting OCT B-scan is due to the anatomy of this eye. We can notice the brighter signal towards the right side of the B-Scan which is at a higher z-position compared to the left side of the B-Scan which has a lower signal since it is at a lower z-position. Note that this is a phenomenon that is seen in most OCT systems. The signal strength decreases as the distance from the zero delay increases. In the example shown, the zero delay is at the top of the B-Scan and hence the signal is expected to be better at the top (higher z-position) with a roll-off towards the bottom (lower z-position). This phenomenon is another reason why it is desirable to obtain the scan with as much reduced tilt as possible so that the A-Scans are uniform in signal characteristics. As shown in FIGS. 11(*c*) and (*d*) it is possible to obtain a B-Scan with reduced tilt over the same region by adjusting the pupil entry position 1102. The intensity across the resulting B-Scan shown in FIG. 11(*d*) is much more uniform than the tilted B-Scan in FIG. 11(*b*).

In order to find the best pupil entry position in this case, the measurement signal is defined as single (or multiple) B-Scans acquired from the same pupil entry position. The B-Scans can then be quickly segmented to determine the tilt in the B-Scan. The tilt would be used as the quality metric and the position that minimizes the tilt can then be selected as the best location for imaging.

One implementation of determining the tilt is with an approximate segmentation of the retinal pigment epithelial layer (RPE), which is usually the brightest layer in the B-Scan. One method to determine this is to find the brightest signal along each A-Scan after smoothing to reduce noise. The different segmented points in the B-Scan are then fit with a line to determine the general tilt of the B-Scan.

Figure 12:
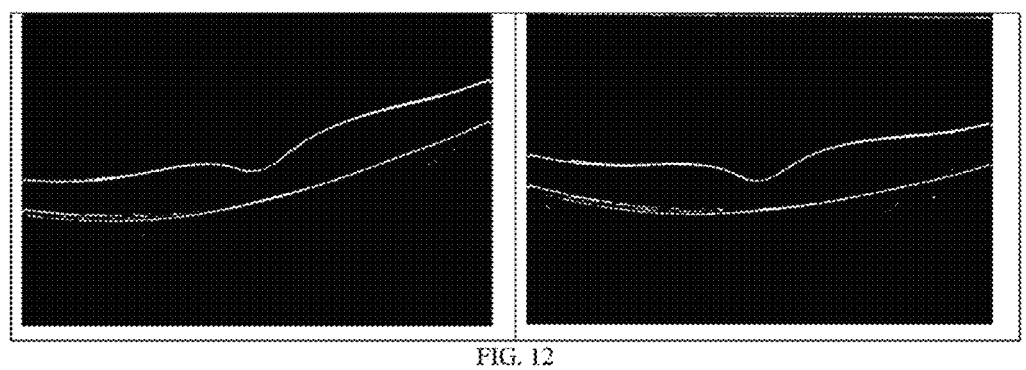
FIG. 12 illustrates how segmentations of the images in FIG. 11 can be used to generate binary masks useful for characterizing the tilt in the data.

In another implementation, a segmentation of the structures of interest might be done based on a calculation of the changes in the intensity along the scan direction (y gradients) and then thresholding them, creating a binary image. The binary image can then be processed to obtain the tilt-angle by fitting a line to the tissue, such as to either the lower or upper boundary of the tissue or to a combination of the two locations, such as the center of the tissue. FIG. 12 shows the binary masks obtained by segmenting the B-Scans shown in FIGS. 11(b) and (d).

Once the tilt of the B-Scan is determined, the optimal pupil entry position that gives the desired tilt of the B-Scan can be selected as the pupil entry position to be used. It has to be noted that the retinal tracking part of the gaze-tracking system can help to acquire the B-Scan over the same region of the retina irrespective of the pupil-entry position. Hence the combination of the methods described in this invention with a retinal tracking system of the type described in the commonly owned pending U.S. application Ser. No. 13/433, 127, filed Mar. 28, 2012, allows the user to acquire data at a particular spot from the retina while taking advantage of the optimal pupil entry position for the application of interest.

Finding the Optimal Pupil Entry Position for Imaging Different Structures

The method described in this invention can also be extended to potentially better visualize different structures in the retina including but not limited to layers such as Henle's fiber layer, Retinal Nerve Fiber Layer, different membranes, vitreous structures, cornea, sub-RPE structures, and the choroid using an OCT system. This is because different structures are visualized differently in OCT based on the orientation of the measurement beam relative to the structure of interest.

For example, the Henle's fiber layer is visualized the best when the OCT beam is perpendicular to the fibers in this layer (see for example Lujan, et al. "Revealing Henle's Fiber Layer using Spectral Domain Optical Coherence Tomography" *Investigative Ophthalmology & Visual Science* 52(3) March 2011 1486-1492). This is because the directional nature of these fibers produces the maximum scattering when they are perpendicular to the beam. This kind of behavior is also true for other layers in the retina such as the retinal nerve fiber layer.

When we are trying to visualize a particular region of interest, using the methods described earlier, we could optimize for the maximum signal from that layer (given that we know the approximate location in the A-Scan or B-Scan of the signal of interest). We could also select the pupil position based on the geometric orientation that would give the best signal for the tissue of interest. Furthermore, imaging through the same location in the pupil at each visit will lead to less variability in the intensity of any directionally reflective layers that are imaged. Quantitative segmentations of layers such as the RNFL may be affected by directional reflectivity, such that variability in pupil entry point from visit to visit increases the variability in the quantitative measurements. A common pupil entry point used at every visit should improve the reproducibility of such measurements. It is also possible that a quality metric that is a function of multiple measures of quality could be used (e.g., Q=signal to noise ratio times a measure of uniformity, or SNR*(1-tilt), or that a set of rules for selecting the quality metric to be optimized could be implemented (e.g., accept up to 3 dB loss of signal in order to obtain a flatter image, but no more).

Hence using the methods described in this invention, it will be possible to select the best pupil entry position for imaging a particular structure of interest. A detailed description for this aspect of the invention will now be described.

Angle Dependent Layer Contrast

In one embodiment that uses many of the aspects of the pupil tracking system described above, retinal OCT images are acquired through multiple points in the pupil. An automated movement of the OCT beam relative to the patient's pupil allows acquisitions at measurable, and preferably pre-determined, positions in the patient's pupil. The movement may be achieved by various means, such as moving the patient's eye relative to the instrument, by moving the instrument relative to the patient's eye, by translating a portion of the instrument like an optical subsystem, or by moving the beam such as with a tilted block of glass that is moved into and out of the path. A manual adjustment can be regulated or guided by typical physical constraints such as detent positions or a hand-operated lever with pre-set motion range. The relative angle of incidence can be determined from the ratio of distance moved in the pupil divided by a typical focal length of the eye, or by accounting for the individual eye length obtained by a convenient method, such as measured axial length or inferred from correlation of refractive error to eye length. The actual movement relative to the patient pupil can be approximated by a measurement of the motion of the patient's head or of the instrument. In typical ophthalmic OCT systems, the illumination and collection are usually co-aligned, for example using a common fiber. In this case the angles of incidence and collection are changed together. In a system where the illumination and collection are not co-aligned, the angles can be varied independently of each other using methods obvious to those skilled in the art. Furthermore, a plurality of illumination or collection paths may be implemented for simultaneous measurements. The implementation is described herein assuming co-alignment of illumination and collection for clarity of description and because this is the most common configuration; nevertheless, co-alignment is not required.

When multiple images with multiple angles of incidence are obtained, the images can be compared with each other by several methods, such as image-based registration of the images followed by creation of difference images or ratio images. Alternatively the scattering profile as a function of depth can be extracted at matching points on the image for comparison. In any case, comparison may include pre-processing of the data, such as background subtraction, gain adjustment (for example to compensate for variations in overall brightness between scans), filtering and averaging to reduce noise, and the creation of summary parameters.

The scattering signal varies with the angle of incidence, so algorithms which segment layers can use information about the local angle of incidence of one or more layers to correctly identify layer boundaries. This is illustrated, for example, in the region generally described as being between the retinal pigment epithelium and the outer plexiform layer (RPE and OPL). In this region, the boundaries between bright and dark layers depend on the angle of incidence. As described above, as the angle of incidence changes, the apparent tilt of the retina in the B-scan changes.

FIGS. 13(a) and (b) show two OCT images. They are both taken at the same location, but with different angles of incidence to the retina. FIG. 13(a) is captured with the scan beam about 5-10 degrees from one side of the normal, and FIG. 13(b) is captured with the scan beam at an angle with a similar magnitude but from the opposite side of the normal. The two images have been registered to each other by measuring and then correcting for differences in the tilt and relative position of tissue in the B-scans. The scattering between "RPE" and "OPL" increases on the side of the retina that appears farther from the incident light than the fovea (left side in FIG. 13(a) denoted by arrow 1301 and right side in FIG. 13(b) denoted by arrow 1302). On the opposite side of the fovea, the scattering is reduced and appears to come from a thinner layer (arrows 1303 and 1304). Thus, it is the angle of incidence, not an asymmetry in the tissue, which causes the effect. As described by Lujan et al, this layer of increased scattering is attributed to Henle's fiber layer (HFL). In this region, an algorithm will attribute the boundary between bright and dark bands to a transition between one pair of layers if the angle of incidence is such that the region appears thicker and to a transition between another pair of layers if the angle of incidence is such that the region appears thinner. The algorithm can obtain this information about the relative angle of incidence from various means, including information about the position of the OCT scan beam in the pupil or by the tilt of the retina in the B-scan as measured either globally or locally. In the case of retinal pathology where local tissue layers are distorted and their orientation is substantially different from the bulk of the retina, a local measurement of the tilt may be more appropriate.

Figure 13:
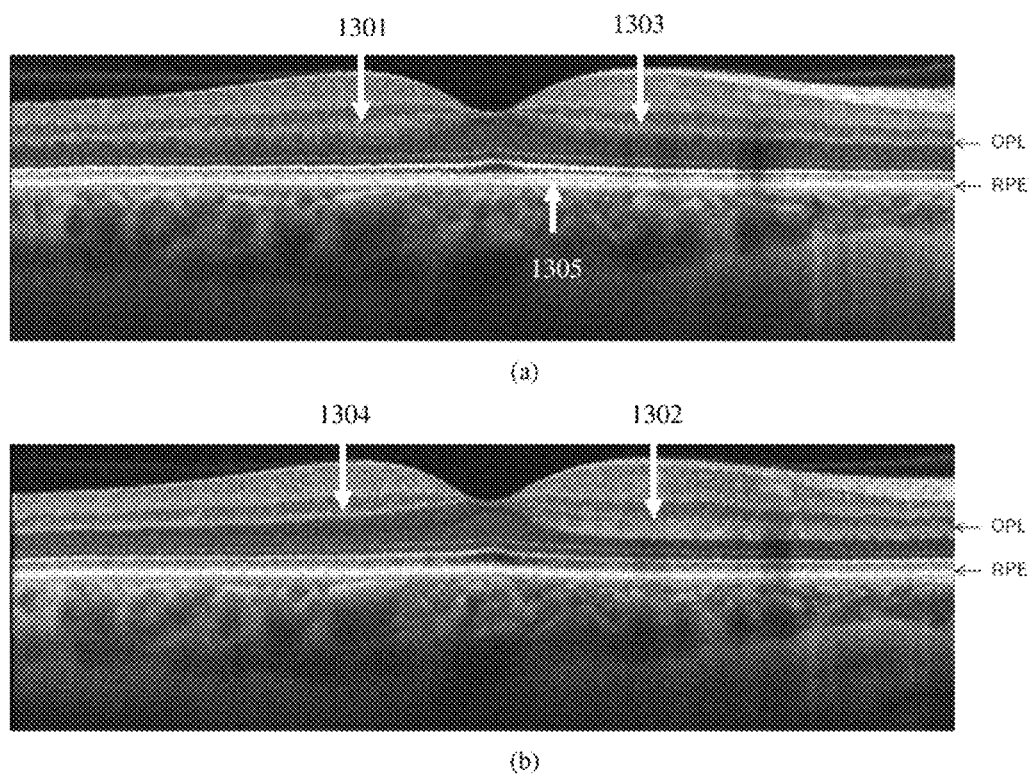
FIGS. 13(a) and (b) show the angle dependent layer contrast that can result when two B-scans are taken at different angles of incidence.

In some cases, the layers of interest can be observed at all angles, even if the gradients in intensity are different depending on the angle. In other cases, the layer of interest may not be differentiated when imaged at a given incident angle. In FIG. 13, there is a layer above the RPE that is apparent in 13(a), but not seen in 13(b) as illustrated by arrow 1305. This layer represents the interdigitation of the RPE with the inner segments of the photoreceptors. If this layer is of interest, it is necessary to find angles at which it can be imaged. Alternately, the boundaries of the HFL can be seen in both 13(a) and 13(b), although the intensity characteristics are very different. To segment this layer it might be sufficient to know the local angle of incidence relative to the fibers. Finally, when the angle of incidence and its effect on tissue reflectivity is known, then the reflectivity may become a useful aspect of anatomy or pathology subject to measurement. That is, if the reflectivity is variable and depends on an unknown angle of incidence, it is difficult to tell if a tissue is poorly imaged or absent. If factors that depend on image setup have been controlled for, the reflectivity may become a useful indicator of health or disease of a given tissue. Examples include detecting glaucomatous damage by evaluating reduced reflectivity of the retinal nerve fiber layer, using the reflectivity of the contents of pigment epithelial detachments to determine the nature or cause of the detachment, and using the reflectivity observed in the outer nuclear layer to evaluate disruptions in the retina.

Figure 14:
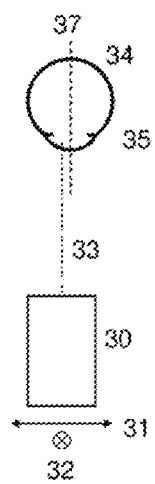
FIG. 14 shows how the measurement system can be translated relative to the eye of a patient to achieve different measurement and hence different angle of incidence imaging.

The OCT images can be obtained with a variety of optical configurations, such as dedicated OCT scanner, an SLO device, through a surgical microscope, or a slit-lamp mounted OCT among others. The above text clearly states that the beam should be moved relative to the pupil to change the angle of incidence. FIG. 14 further clarifies this by showing one example approach. Scan beam 33 is moved relative to eye. In this embodiment, the measuring module 30, which could be for example, just part of scan head, entire instrument, or some subset of the instrument that controls position of the scan beam, is translated along direction 31 so that beam moves relative to the eye, shown here as the approximate axis of the eye 37 to scan the posterior pole 34. Entry points are limited by the pupil boundary 35. This can also be done in the plane 32 perpendicular to the drawing plane. An example of determining the relative angle of incidence from the beam position is to detect the position of the beam 33 relative to the pupil 35 by means such as a CCD camera. The movement does not need to be a pure translation of measuring module 30 as long as the position of the beam 33 relative to the pupil boundary 35 is changed. If the distance from measuring module 30 to pupil boundary 35 is sufficiently large then the position of the beam at the pupil boundary 35 can be changed with only minor changes to the angle of incidence at the retina by rotating measuring module 30 to move the position of the beam in the pupil plane.

Figure 15:
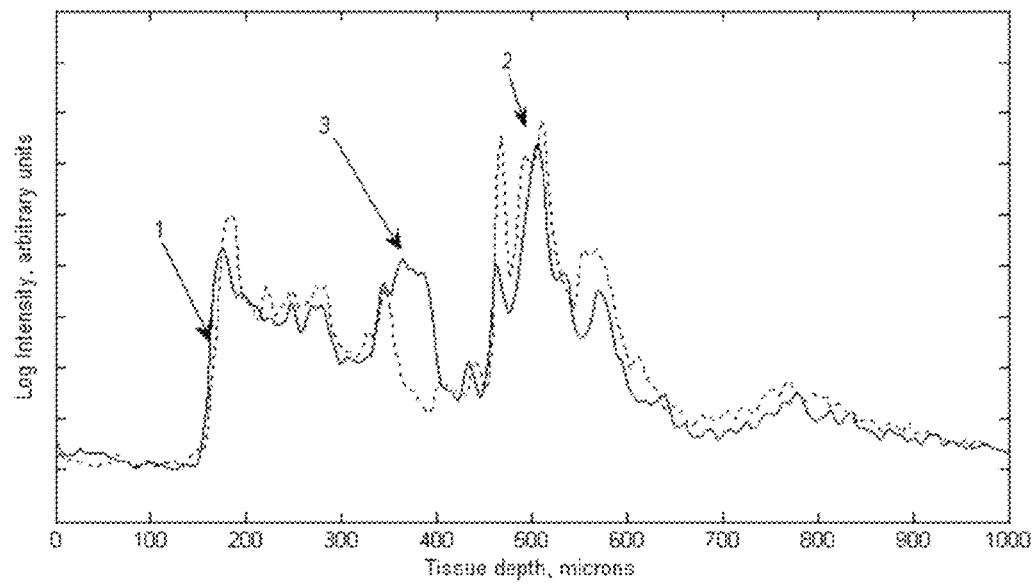
FIG. 15 shows one way to compare the intensities of B-scans taken at different angles of incidence.

This method has been used to make such measurements with a Cirrus OCT (Carl Zeiss Meditec, Inc. Dublin, Calif.). Images have been analyzed in several ways, both by image registration and comparison of intensity profiles. FIG. 15 shows a plot of intensity profiles from two separate B-scans taken from the same region of the retina but with angles of incidence that vary by approximately 15 degrees based on calculations of beam position in the pupil as described above. Features commonly referred to as the inner limiting membrane (ILM) 1, and retinal pigment epithelium (RPE) layer 2 are indicated in the plot. The scattering intensity is different between the two scans due to differences in the angle of incidence of the scanning beam on the tissue. For example, scattering intensity is higher at point 3.

Figure 16:
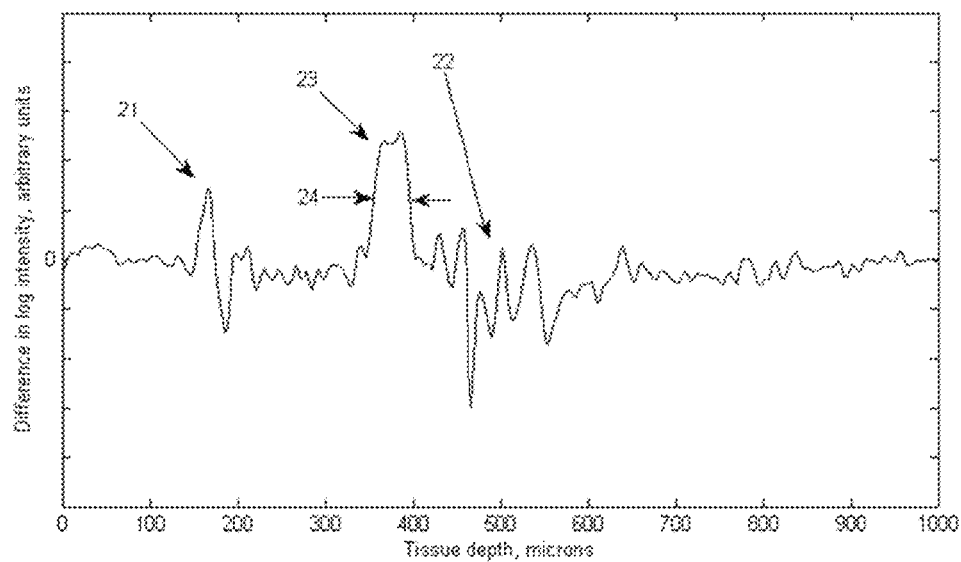
FIG. 16 shows an alternative way to compare the intensities of B-scans taken at different angles of incidence by subtracting one of the intensities from the other.

As described above, the intensity between images can also be compared, for example, by subtracting the two profiles from each other as shown in FIG. 16. Locations 21, 22 and 23 correspond to locations 1, 2, and 3, respectively, in FIG. 15. The difference between the two profiles is caused by measurement noise, registration errors, and repeatable differences due to different angles of incidence. For example, the existence of region 23 is due to a difference in the angles of incidence. Using this difference as a contrast mechanism, the thickness 24 of the tissue whose contrast changes can be measured.

Figure 17:
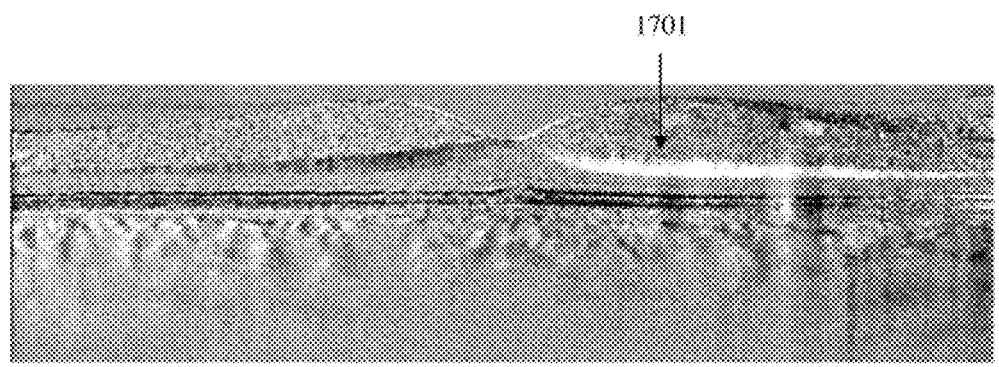
FIG. 17 shows another alternative way to compare the intensities of B-scans taken at different angles of incidence by subtracting one of images from the other.

Similar analyses can be performed on entire OCT B-scans. FIG. 17 shows the resulting difference image generated by subtracting the two scans shown in FIGS. 13(a) and (b), one from the other. The difference image highlights differences in scattering due to angle of incidence of the OCT scan as indicated by arrow 1701.

Figure 18:
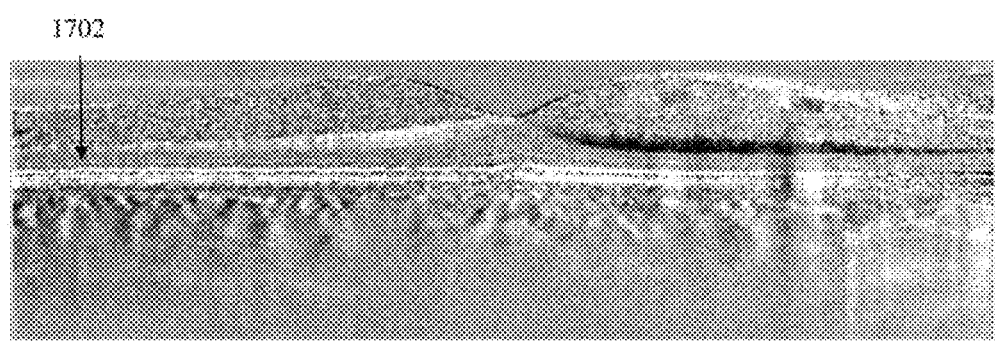
FIG. 18 shows another alternative way to compare the intensities of B-scans taken at different angles of incidence by subtracting one of images from the other in the opposite order of the subtraction in FIG. 17.

The difference image can be displayed in variations, such as color. For black and white viewing, the negative image, formed by subtracting the images in the opposite order can be useful as well. FIG. 18 shows how regions that are difficult to see in FIG. 17 can be visualized more clearly, one example of which is indicated by arrow 1702.

The preferred embodiment encompasses an automated process whereby OCT images are collected at multiple angles of incidence, the images are registered to each other, and processed either by subtraction of B-scans or intensity distributions to identify and determine the thickness of specific layers with angle dependent intensity.

Opacity Mapping

An additional aspect of the present invention is the ability to provide an opacity map of the pupil of a patient to a clinician that highlights regions of opacity such as cataracts and further give insights into the "denseness" of the opacity The main components of this invention are an imaging means to obtain an image of the eye, a processing unit to segment the boundaries of the pupil and a unit to track the gaze of the eye and a measurement unit that measures some property of the eye by sending an optical beam through the pupil. The invention is general and can work with any type of pupil segmentation and gaze tracking.

Figure 19:
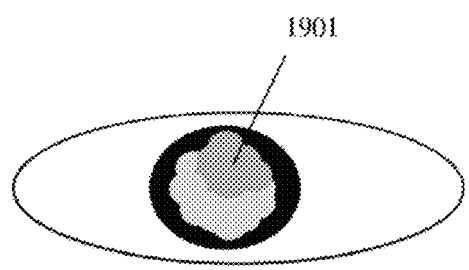
FIG. 19 illustrates how opacity of the eye can be visualized using an embodiment of the present invention.

As the first step, the boundaries of the pupil are segmented. Using the segmentation of the pupil, it is possible to make the measurement beam pass through different points on the pupil automatically. The resulting signals can be analyzed to find the quality of the measurement signal. For example, in an OCT system, the quality could be the signal strength of the acquired OCT A-Scan or B-Scan. The quality of the measurement signal is usually inversely related to the opacity. The beam entry position can be varied over a grid and a mapping of the opacity can be obtained since the quality of the measurement signal corresponds to the opacity at the corresponding beam entry position. One example of such a mapping is shown in FIG. 19. Darker shading as visible in the top right part of the image 1901 means there is more opacity.

Although various embodiments that incorporate the teachings of the present invention have been shown and described in detail herein, those skilled in the art can readily devise many other varied embodiments that still incorporate these teachings.

The following references are hereby incorporated by reference:

Patent Documents

US Patent Publication No. 2005/0024586 Teiwes et al. "Multidimensional eye tracking and position measurement system for diagnosis and treatment of the eye"

US Patent Publication No. 2007/0291277 Everett et al. "Spectral domain optical coherence tomography system"

U.S. Pat. No. 7,805,009 Everett et al. "Method and apparatus for measuring motion of a subject using a series of partial images from an imaging subject"

U.S. patent application Ser. No. 13/433,127, filed Mar. 28, 2012, Iyer et al. "Systems and methods for efficiently obtaining measurements of the eye using tracking"

Non-Patent Literature

Lujan et al. "Henle's Fiber layer revealed using spectral domain optical coherence tomography" ARVO abstract #1201 2010.

Lujan, et al. "Revealing Henle's Fiber Layer using Spectral Domain Optical Coherence Tomography". *Investigative Ophthalmology & Visual Science* 52(3) March 2011 1486-1492.

Liao et al. "Robust Pupil Detection for Gaze-Based User Interface" EGIHMI '10 Proceedings of the 2010 Workshop on Eye Gaze in Intelligent Human Machine Interaction.

Zhu et al. "Robust Pupil Detection using a Curvature Algorithm" *Computer Methods and Programs in Biomedicine* 59 (1999) 145-157.

Li et al. "Starburst: A hybrid algorithm for video-based eye tracking combining feature-based and model-based approaches" Vision for Human-Computer Interaction Workshop (in conjunction with CVPR), 2005.

Leitgeb et al., "Ultrahigh resolution Fourier domain optical coherence tomography," *Optics Express* 12(10):2156 2004

Choma et al. (2003). "Sensitivity advantage of swept source and Fourier domain optical coherence tomography." *Optics Express* 11(18): 2183-2189

What is claimed is:

1. A method for analyzing Optical Coherence Tomography (OCT) measurement data of a tissue in an eye, said OCT measurement data acquired using an OCT device including an OCT measurement beam for illuminating the tissue through a plurality of pupil entry locations, the method comprising:
    acquiring a first OCT measurement of a region of tissue in the eye when the measurement beam enters the eye at a first pupil entry position;
    acquiring a second OCT measurement of said region tissue in the eye when the measurement beam enters the eye at a second pupil entry position different from the first pupil entry position;
    comparing the first and second OCT measurements to identify a tissue characteristic based on the differences in the measurements resulting from the different pupil entry positions; and
    storing or displaying information corresponding to the identified tissue characteristic.

2. A method as recited in claim 1, in which the OCT measurements are A-scans.

3. A method as recited in claim 2, in which comparing step includes subtracting the intensity profile of the second A-scan from the intensity profile of the first A-scan.

4. A method as recited in claim 1, in which the OCT measurements are B-scans.

5. A method as recited in claim 4, in which the comparing step includes registering the first and second B-scans.

6. A method as recited in claim 5, in which the comparing step further includes generating a difference image by subtracting the registered B-scans.

7. A method as recited in claim 1, in which the tissue characteristic is a layer boundary in the tissue.

8. A method as recited in claim 1, in which the tissue characteristic is a layer thickness in the tissue.

9. A system for obtaining and analyzing measurement data of a region of tissue in an eye, said system comprising:
    a light source for generating a beam of light;
    a splitting element for splitting the beam of light into reference and sample arms;
    optics for directing the light in the sample arm to one or more locations on the eye tissue;
    means for adjusting the pupil entry position of the beam of light on the pupil of the eye;
    a detector for receiving interfering light from the sample and reference arms and generating signals in response thereto; and
    a processor for converting the signals into measurement data, said processor further for comparing OCT measurement data of the same tissue region collected at two different pupil entry positions to identify a tissue characteristic based on the differences in the measurements resulting from the different pupil entry positions.

10. A system as recited in claim 9, in which the measurement data are A-scans.

11. A system as recited in claim 10, in which the measurement data are B-scans.

12. A system as recited in claim 10, in which the tissue characteristic is a layer boundary.

13. A system as recited in claim 9, in which the tissue characteristic is a layer thickness.

14. A system as recited in claim 9, further comprising a display for displaying the identified tissue characteristic or a further analysis thereof.

15. A system as recited in claim 9, in which the comparing includes subtracting one of the measurements from the other.

16. A system as recited in claim 9, in which the means for adjusting the pupil entry position is a motion of the instrument relative to the patient.

17. A system as recited in claim 9, in which the means for adjusting the pupil entry position is an insertable optic in the beampath of the light traveling to the tissue.

18. A system as recited in claim 9, in which the means for adjusting the pupil entry position is a motion of a portion of the system relative to the patient.

\* \* \* \* \*

UNITED STATES PATENT AND TRADEMARK OFFICE
CERTIFICATE OF CORRECTION

PATENT NO. : 9,918,634 B2
APPLICATION NO. : 14/712121
DATED : March 20, 2018
INVENTOR(S) : Harihar Narasimha-Iyer et al.

Page 1 of 1

It is certified that error appears in the above-identified patent and that said Letters Patent is hereby corrected as shown below:

In the Claims

In Column 14, Line 53, after "opacity" insert -- . --.

Signed and Sealed this
Thirty-first Day of July, 2018

Andrei Iancu
*Director of the United States Patent and Trademark Office*